United States Patent
Prest et al.

(10) Patent No.: US 8,655,004 B2
(45) Date of Patent: Feb. 18, 2014

(54) SPORTS MONITORING SYSTEM FOR HEADPHONES, EARBUDS AND/OR HEADSETS

(75) Inventors: Christopher Prest, San Francisco, CA (US); Quin C. Hoellwarth, Kuna, ID (US)

(73) Assignee: Apple Inc., Cupertino, CA (US)

( * ) Notice: Subject to any disclaimer, the term of this patent is extended or adjusted under 35 U.S.C. 154(b) by 1031 days.

(21) Appl. No.: 12/196,182

(22) Filed: Aug. 21, 2008

(65) Prior Publication Data

US 2009/0097689 A1    Apr. 16, 2009

Related U.S. Application Data

(60) Provisional application No. 60/980,381, filed on Oct. 16, 2007.

(51) Int. Cl.
*H04R 25/00* (2006.01)

(52) U.S. Cl.
USPC .......................................................... 381/380

(58) Field of Classification Search
USPC .......................................................... 381/380
See application file for complete search history.

(56) References Cited

U.S. PATENT DOCUMENTS

| | | | |
|---|---|---|---|
| 5,844,816 A * | 12/1998 | Inanaga et al. ................ 702/145 |
| 6,466,673 B1 * | 10/2002 | Hardy .......................... 381/71.6 |
| 6,738,485 B1 * | 5/2004 | Boesen ......................... 381/312 |
| 6,898,550 B1 | 5/2005 | Blackadar |
| 7,209,775 B2 * | 4/2007 | Bae et al. ...................... 600/340 |
| 7,489,979 B2 * | 2/2009 | Rosenberg ....................... 700/94 |
| 7,565,179 B2 * | 7/2009 | Hyatt ........................ 455/569.1 |
| 2002/0022551 A1 * | 2/2002 | Watterson et al. ................ 482/8 |
| 2004/0225207 A1 * | 11/2004 | Bae et al. ...................... 600/340 |
| 2004/0243416 A1 * | 12/2004 | Gardos ......................... 704/275 |
| 2005/0238207 A1 * | 10/2005 | Tavares ........................ 382/115 |
| 2006/0107822 A1 | 5/2006 | Bowen |
| 2007/0028370 A1 * | 2/2007 | Seng ................................ 2/410 |
| 2007/0079027 A1 | 4/2007 | Marriott et al. |
| 2007/0197881 A1 * | 8/2007 | Wolf et al. .................... 600/300 |
| 2007/0230736 A1 * | 10/2007 | Boesen ......................... 381/380 |
| 2007/0270663 A1 | 11/2007 | Ng et al. |
| 2007/0270721 A1 | 11/2007 | Ananny |
| 2007/0271065 A1 | 11/2007 | Gupta et al. |
| 2007/0271116 A1 | 11/2007 | Wysocki |
| 2007/0271387 A1 | 11/2007 | Lydon |
| 2007/0297618 A1 * | 12/2007 | Nurmi et al. ................. 381/71.6 |
| 2008/0076972 A1 * | 3/2008 | Dorogusker et al. ......... 600/300 |
| 2008/0132798 A1 * | 6/2008 | Hong et al. ................... 600/508 |

(Continued)

FOREIGN PATENT DOCUMENTS

| | | | |
|---|---|---|---|
| GB | 2396421 | * | 6/2004 |
| WO | WO 95/13690 | * | 5/1995 |
| WO | WO 2007/013054 | * | 3/2007 |

*Primary Examiner* — A. Sefer
(74) *Attorney, Agent, or Firm* — Fish & Richardson P.C.

(57) ABSTRACT

A monitoring system that can be placed proximate to the head or ear of a user is disclosed. According to one embodiment, the monitoring system can be used with headphones, earbuds or headsets. The monitoring system can, for example, be used to monitor user activity, such as during exercise or sporting activities. The positioning of the monitoring system can also facilitate sensing of other user characteristics (e.g., biometric data), such as temperature, perspiration and heart rate. The monitoring system can also be used to control a an electronic device. In one embodiment, the monitoring system facilitates user control of the electronic device using head gestures.

20 Claims, 5 Drawing Sheets

(56) References Cited

U.S. PATENT DOCUMENTS

| | | |
|---|---|---|
| 2008/0165017 A1* | 7/2008 | Schwartz .................... 340/573.1 |
| 2008/0187163 A1* | 8/2008 | Goldstein et al. ............. 381/380 |
| 2008/0211768 A1* | 9/2008 | Breen et al. ................... 345/157 |
| 2008/0255430 A1* | 10/2008 | Alexandersson et al. ..... 600/300 |
| 2009/0010461 A1* | 1/2009 | Klinghult et al. ............. 381/309 |
| 2009/0082994 A1* | 3/2009 | Schuler et al. ................ 702/160 |
| 2009/0105548 A1* | 4/2009 | Bart .............................. 600/300 |
| 2009/0287067 A1* | 11/2009 | Dorogusker et al. ......... 600/300 |
| 2011/0125063 A1* | 5/2011 | Shalon et al. ................. 600/590 |

* cited by examiner

SPORTS MONITORING SYSTEM FOR HEADPHONES, EARBUDS AND/OR HEADSETS

CROSS-REFERENCE TO RELATED APPLICATION

This application claims priority to U.S. Provisional Patent Application No. 60/980,381, filed Oct. 16, 2007, entitled "Sports Monitoring System for Headphones, Earbuds and/or Headsets", which is herein incorporated herein by reference.

BACKGROUND OF THE INVENTION

Conventionally, pedometers have been worn (e.g., attached to a wrist or to a user's hip) to monitor and display a distance traveled by a user. More recently, accelerometers have been provided within a user's shoe to measure distance and speed traveled by the user while walking or running. As one example, as explained in U.S. Pat. No. 6,898,550, a foot-mounted sensor can sense motion and wirelessly transmit sensor data to a wrist-mounted unit. As another example, a sports monitoring product (Nike+iPod) available from Apple Inc. can be utilized with a digital media player to monitor distance and speed of its user. The sports monitoring product includes a module that is placed within a shoe of the user, and the digital media player operates to wirelessly communicate with the module so that the distance and speed of the user can be displayed by the digital media player.

SUMMARY OF THE INVENTION

The invention pertains to a monitoring system that can be placed proximate to the head or ear of a user. According to one embodiment, the monitoring system can be used with a hearing device, headphones, earbuds or headsets. The monitoring system can, for example, be used to monitor user activity, such as during exercise or sporting activities. The positioning of the monitoring system can also facilitate sensing of other user characteristics (e.g., biometric data), such as temperature, perspiration and heart rate.

Advantageously, the invention can provide monitoring capabilities within a hearing device. Assuming the user is otherwise using the hearing device, such as to provide audio output by a portable media player, the user gains monitoring capabilities without requiring the user to wear or carry an additional article.

In one embodiment, a monitoring system is integrated with headphones, earbuds or headsets. In another embodiment, the monitoring system can be coupled to headphones, earbuds or headsets. For example, when not integrated with the headphones, earbuds or headsets, the monitoring system can be coupled to the headphones, earbuds or headsets by a mechanical member. Also, the monitoring system can be attachable/detachable from the headphones, earbuds or headsets. In still another embodiment, the monitoring system can be provided within a housing attached to a cord utilized by the headphones, earbuds or headsets. In yet another embodiment, the monitoring system can be attached to a user's clothing. In these various embodiments, the headphones, earbuds or headsets can be wired or wireless.

The monitoring system can also be used to control a device connected to the headphones, earbuds or headsets. The device being controlled can be a stationary device or mobile device. As examples, the device can pertain to a telephone, digital media player, etc.

The invention may be implemented in numerous ways, including, but not limited to, as a system, device, apparatus, or method. Example embodiments of the present invention are discussed below.

As a hearing device, one embodiment of the invention can, for example, include at least: an audio output device; and a monitoring system configured to monitor user activity. The monitoring system can comprise at least one accelerometer, and the audio output device can comprise a speaker. Further, the hearing device can be embodied as an earbud, a headset or headphones.

As an earbud for use by a user to receive audio sound, one embodiment of the invention can, for example, include at least: an ear interface portion configured to be placed within or proximate to the ear of the user; a speaker configured to produce audible sound that is provided to the ear of the user via said ear interface portion; and an activity sensor configured to monitor user activity.

As a method for controlling an electronic device though one or more head gestures, one embodiment of the invention can, for example, include at least: receiving head motion data pertaining a head motion of a user of the electronic device; determining whether the head motion data matches any of a plurality of predetermined head gestures; and identifying an action associated with the matching predetermined head gesture. Additionally, the method can further operate to perform the identified action on the electronic device.

Various aspects and advantages of the invention will become apparent from the following detailed description taken in conjunction with the accompanying drawings which illustrate, by way of example, the principles of the invention.

BRIEF DESCRIPTION OF THE DRAWINGS

The invention will be readily understood by the following detailed description in conjunction with the accompanying drawings, in which.

DETAILED DESCRIPTION OF THE INVENTION

Exemplary embodiments of the present invention are discussed below with reference to the various figures. However, those skilled in the art will readily appreciate that the detailed description given herein with respect to these figures is for explanatory purposes, as the invention extends beyond these embodiments.

The invention pertains to a monitoring system that can be placed proximate to the head or ear of a user. According to one embodiment, the monitoring system can be used with a hearing device, headphones, earbuds or headsets. The monitoring system can, for example, be used to monitor user activity, such as during exercise or sporting activities. The monitoring system can also facilitate sensing of other user characteristics (e.g., biometric data), such as temperature, perspiration and heart rate.

Advantageously, the invention can provide monitoring capabilities within a hearing device. Assuming the user is otherwise using the hearing device, such as to provide audio output by a portable media player, the user gains monitoring capabilities without requiring the user to wear or carry an additional article.

In one embodiment, a monitoring system is integrated with headphones, earbuds or headsets. In another embodiment, the monitoring system can be coupled to headphones, earbuds or headsets. For example, when not integrated with the headphones, earbuds or headsets, the monitoring system can be coupled to the headphones, earbuds or headsets by a mechanical member. Also, the monitoring system can be attachable/detachable from the headphones, earbuds or headsets. In still another embodiment, the monitoring system can be provided within a housing attached to a cord utilized by the headphones, earbuds or headsets. In yet another embodiment, the monitoring system can be attached to a user's clothing. In these various embodiments, the headphones, earbuds or headsets can be wired or wireless.

The monitoring system can also be used to control a device coupled to the headphones, earbuds or headsets. The device being controlled can be a stationary device or a mobile device. As examples, the device being controlled can pertain to a telephone, digital media player, etc. In one embodiment, the monitoring system facilitates user control of the device using head gestures.

Embodiments of the invention are discussed below with reference to FIGS. 1A-3. However, those skilled in the art will readily appreciate that the detailed description given herein with respect to these figures is for explanatory purposes as the invention extends beyond these limited embodiments.

Figure 1A:
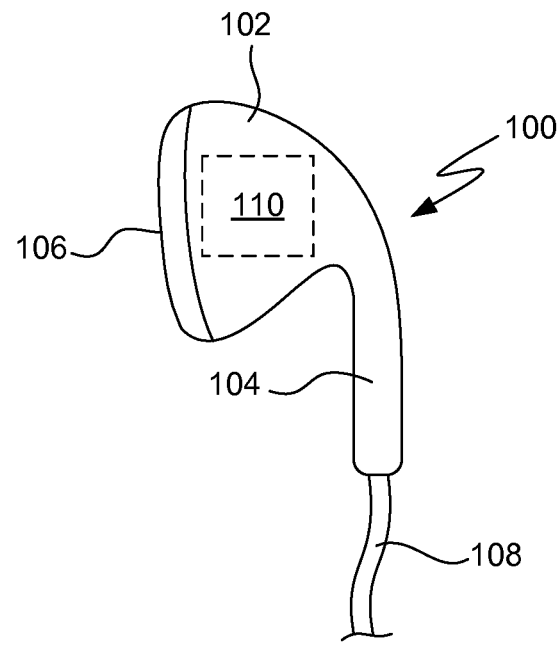
FIG. 1A is an exemplary diagram of an earbud according to one embodiment of the invention.

FIG. 1A is an exemplary diagram of an earbud 100 according to one embodiment of the invention. The earbud 100 can output audible sounds for a user. The earbud 100 can also provide or assist in providing activity monitoring.

The earbud 100 includes an upper portion 102, a base portion 104 and an ear interface portion 106. During use, the ear interface portion 106 is placed within or proximate to the ear of a user. The upper portion 102 typically includes an audio output speaker that produces audible sound that is provided to the user's ear via the ear interface portion 106. The base portion 104 supports the upper portion 102 and typically couples the earbud 102 to a cord 108. In addition, the earbud 100 can include an activity sensor 110 integrated with the earbud 100. As illustrated in FIG. 1A, the activity sensor 110 can be integrated with the upper portion 102 of the earbud 100. However, it should be noted that in an alternative embodiment, the activity sensor 110 can be embedded in the base portion 104 of the earbud 100. In one embodiment, the activity sensor 110 includes at least an accelerometer. In another embodiment, the activity sensor 110 can include a plurality of accelerometers, each pertaining to a different axis.

Figure 1B:
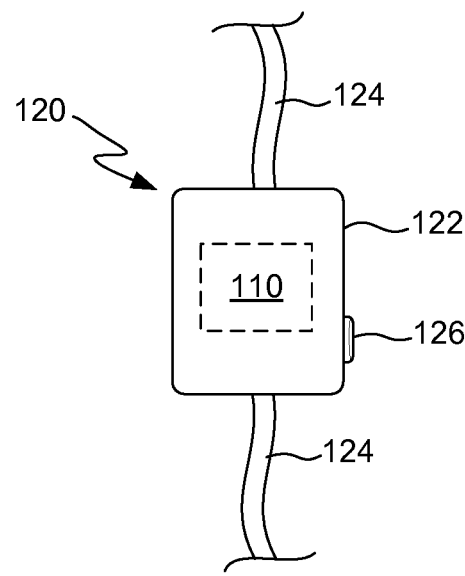
FIG. 1B is an exemplary diagram of a cord-based monitoring system according to one embodiment of the invention.

FIG. 1B is an exemplary diagram of a cord-based monitoring system 120 according to one embodiment of the invention. The cord-based monitoring system 120 can be utilized by headphones, earbuds or headsets that utilize a cord. The cord-based monitoring system 120 can include a sensor housing 122 attached to a cord 124. The sensor housing 122 can include the activity sensor 110. Here, the activity sensor 110 is attached to the cord 124, as opposed to being integrated with the earbud 100 as illustrated in FIG. 1A. Optionally, the cord-based monitoring system 120 can include a user input device 126. For example, the user input device 126 can pertain to a button. The cord-based monitoring system 120 can also include a securing means for securing the cord-based monitoring system 120 to a user's body or clothing. Examples of securing means include Velcro™ (hook and loops), button, pocket, strap, clip, etc.

Figure 1C:
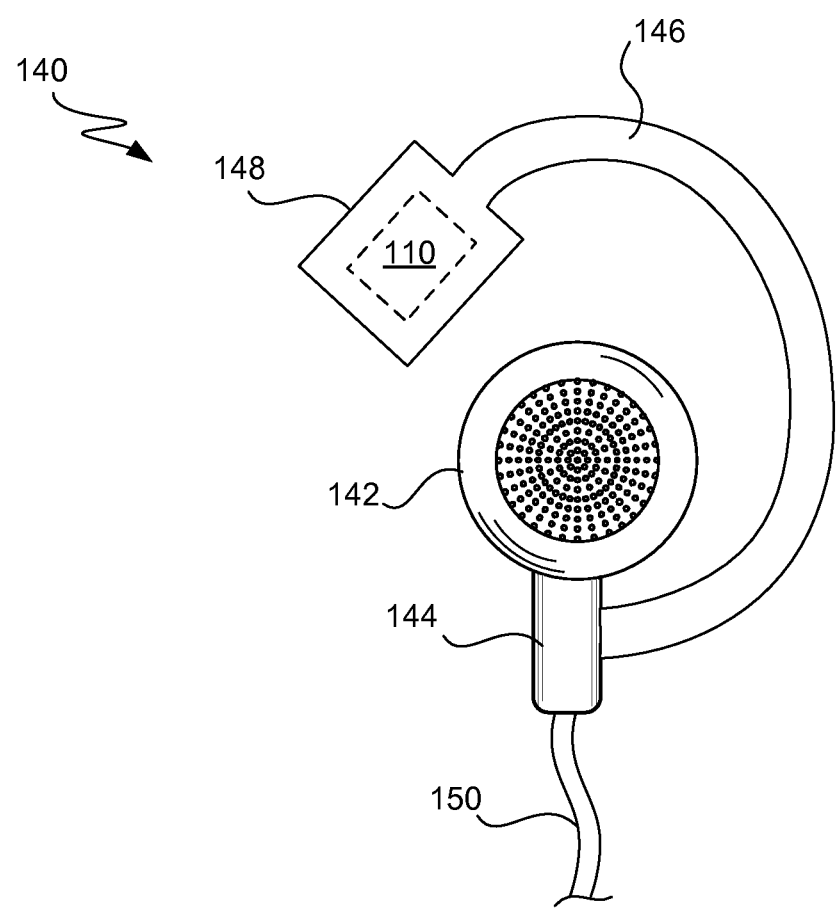
FIG. 1C is an exemplary diagram of an ear-based monitoring system according to one embodiment of the invention.

FIG. 1C is an exemplary diagram of an ear-based monitoring system 140 according to one embodiment of the invention. The ear-based monitoring system 140 includes an earbud 142 having a base portion 144. An attachment member 146 can couple to the base portion 144. The attachment member 146 physically attaches a sensor housing 148 to a location proximate to the user's ear. The sensor housing 148 can include the activity sensor 110. In this embodiment, the activity sensor 110 is positioned proximate to the user's ear by the attachment member 146 as opposed to being attached to the cord 124 as illustrated in FIG. 1B or being integrated with the earbud 100 as illustrated in FIG. 1A.

Figure 1D:
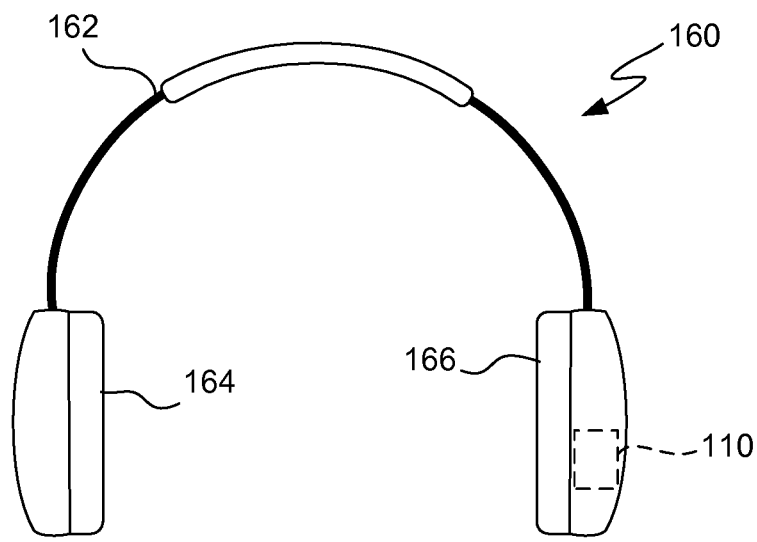
FIG. 1D is an exemplary diagram of a headset according to one embodiment of the invention.

FIG. 1D is an exemplary diagram of a headset 160 according to one embodiment of the invention. The headset 160 includes a support member 162 that supports a first ear interface 164 and a second ear interface 166. The second ear interface 166 can include the activity sensor 110. In one implementation, the activity sensor 110 is integrated within the second ear interface 166.

Figure 1E:
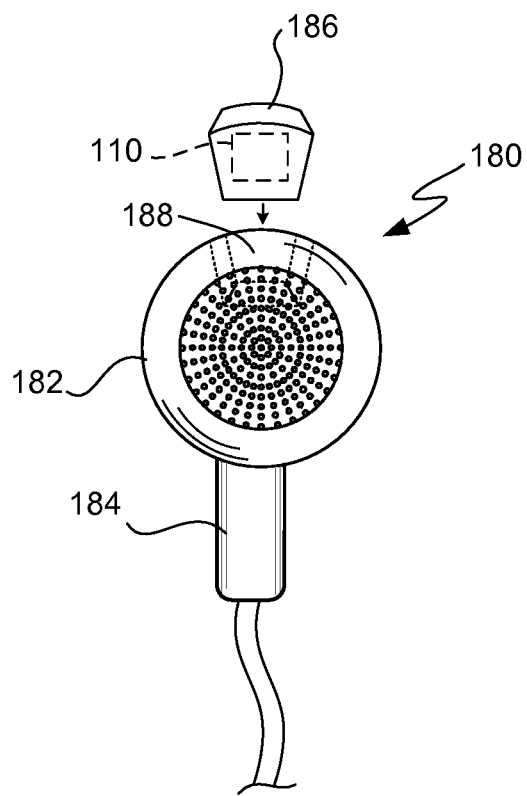
FIG. 1E is an exemplary diagram of an earbud according to one embodiment of the invention.

FIG. 1E is an exemplary diagram of an earbud 180 according to one embodiment of the invention. The earbud 180 can include an upper portion 182 and a lower portion 184. The upper portion 182 can also be referred to as the body of the earbud 180. A detachable portion 186 can be attached or detached from the upper portion 182 via a slot 188 provided within the upper portion 182. The detachable portion 186 can include the activity sensor 110. In one implementation, when the earbud 180 has the detachable portion 186 attached to the upper portion 182 via the slot 188, the activity sensor 110 provided within the detachable portion 186 is effectively integrated with the earbud 180 and can, for example, operate as can the earbud 100 illustrated in FIG. 1. In an alternative embodiment, the detachable portion could be coupled to the lower portion 184 of the earbud 180.

As previously noted, the headphones, earbuds or headsets can be wired or wireless. In the event that the headphones, earbuds or headsets are wireless, then sensor data captured by the activity sensor 110 can also be transmitted wirelessly. Typically, the wireless transmissions are relatively short range, such as less than 20 feet. Bluetooth is one example of short range wireless protocol suitable for use with short range wireless data communications.

Figure 2:
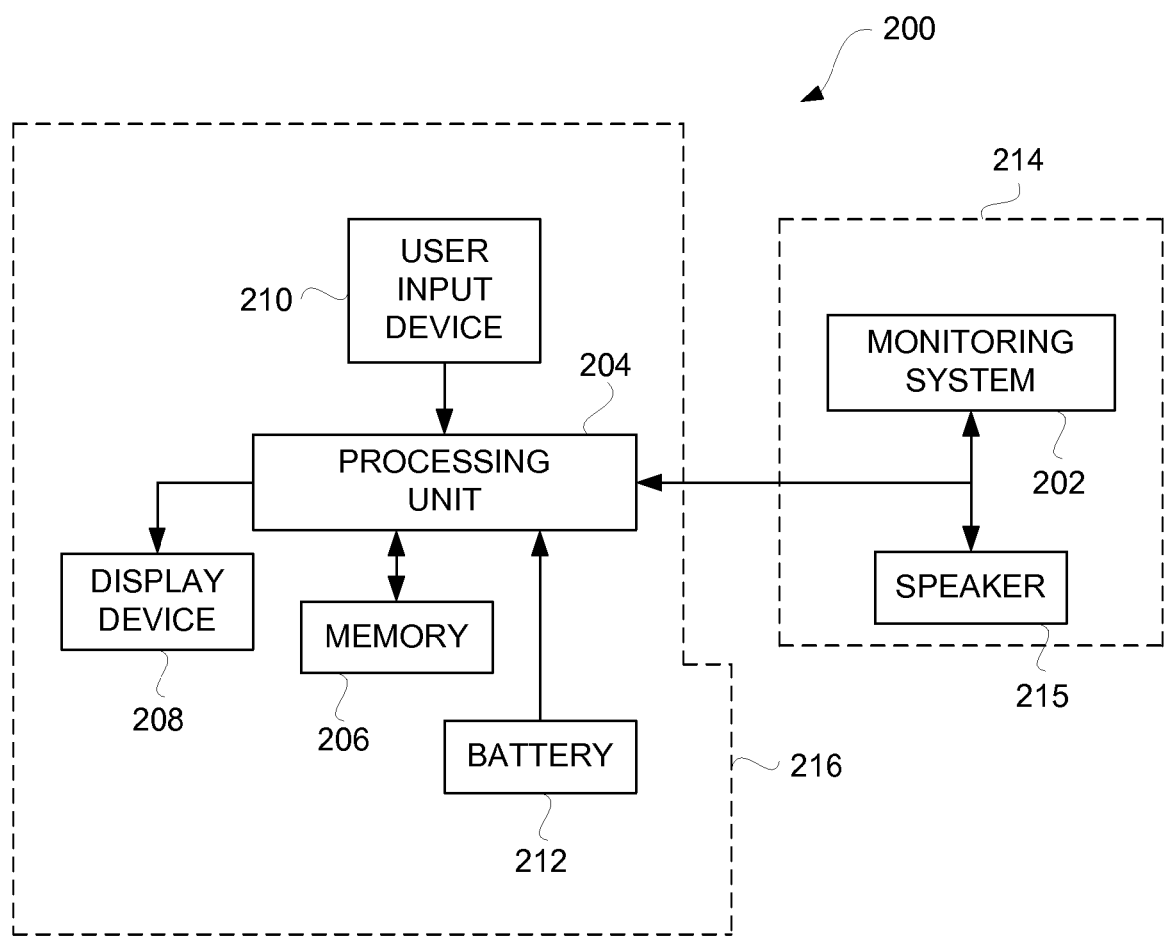
FIG. 2 is a block diagram of an electronic system according to one embodiment of the invention.

FIG. 2 is a block diagram of an electronic system 200 according to one embodiment of the invention. The electronic system 200 includes a monitoring system 202 that monitors physical conditions, such as activity, associated with a user of the electronic system 200. The monitoring system 202 can include at least one sensor that captures monitored data. The monitored data can be supplied to a processing unit 204. The processing unit 204 can pertain to a microprocessor, a controller, an integrated circuit or other circuitry used to process the monitored data. The processing unit 204 can store to and/or retrieve data from a memory 206. The processing unit 204 can also determine an appropriate output, if any, to be display on a display device 208. The electronic system 200 can further include a user input device 210. The user input device 210 can, for example, pertain to one or more of: a touchpad, a keypad, a dial, or a button. The electronic system 200 can also include a battery 212. The battery 212 can allow the electronic system 200 to operate as a portable electronic system.

The monitoring system 202 can include at least one sensor. The sensor can be an activity sensor. In one implementation, the activity sensor can use at least one accelerometer. The accelerometer can be a one-axis or multiple-axis accelerometer. As an example, when the hearing device 214 includes a pair of earbuds, one or both of the earbuds can include one or more accelerometers. In another implementation, the activity sensor can use a plurality of accelerometers. The sensor can also be other than (or in addition to) an activity sensor, such as a psychological or biometric sensors which could measure temperature, heartbeat, etc. of a user of the monitoring system 202. Since sensors can be positioned proximate to the head or ear of the user, useful psychological or biometric data can be acquired. The sensor can also be other than (or in addition to) an activity sensor, such as a global positioning system (GPS) receiver or a proximity sensor.

In one embodiment, such as illustrated in FIG. 2, the monitoring system 202 can be provided in or attached to a hearing device 214. The hearing device 214 includes at least a speaker 215 (more generally, an audio output device) for providing audio sound to a user of the hearing device 214. The hearing device 214 can, for example, pertain to a headphone, earbud or headset. In such an embodiment, the balance of the electronic system 200 (e.g., the processing unit 204, the memory 206, the display device 208, the user input device 210 and the battery 212) can reside with an electronic device 216. In an alternative embodiment, the hearing device 214 can include some additional circuitry. For example, the hearing device 214 could include processing circuitry to at least partially process the monitored data from at least one sensor with the monitoring system 202.

The monitoring system 202 can also be used to control or influence operation of the electronic device 216. The monitoring system 202 can couple to the electronic device 216 via at least one wire (e.g., a cable) or wirelessly (e.g., Bluetooth). For example, if a wire is used the wire can be a dedicated wire or can be a wire that is shared, such as a cord from the electronic device 216 to a headphone, earbud or headset. The electronic device 216 can be controlled can be a stationary device or a mobile device. As examples, the device being controlled can pertain to a telephone, digital media player, personal digital assistant (PDA), etc.

In one implementation, the monitoring system 202 includes merely the at least one sensor. In another implementation, the monitoring system 202 further includes circuitry used to partially or fully process the monitored data from the at least one sensor.

According to another embodiment of the invention, given that there can be an activity sensor proximate to a user's ear or head, the activity sensor can be utilized to control an electronic device (e.g., electronic device 216). For example, if the electronic device is a mobile media playback device, then the movement of the user's head can be utilized to invoke commands for the media playback device. For example, moving one's head in a predetermined manner can be considered as a gesture. In the case of the media playback device such a gesture can cause play, pause, next, back, skip, volume up, or the volume down. Table I provides some exemplary gestures.

| Gesture | Command |
|---|---|
| Tilt head left | Next item forward |
| Tilt head right | Next item backwards |
| Rotate head right | Increase volume |
| Rotate head left | Decrease volume |

-continued

| Gesture | Command |
|---|---|
| Tilt head forward | Play |
| Tilt head backward | Pause |

To simplify user input gestures and/or processing therefore, a gesture can be combined with a user input action (e.g., button action). For example, if a cord for headphones, earbuds or headsets include an user input device (e.g., user input device 126), the user input device 126 (e.g., button) can be activated (e.g., pressed) while (or immediately prior or immediately after) the gesture is being performed. This allows the device to understand when it receives a gesture intended to cause a user control of some feature of the electronic device.

More generally, gestures, such as head gestures, can be used as inputs to an electronic device. Sensors (e.g., accelerometer, gyroscope, motion sensor) provided proximate the user's ear or head can be used to detect, pitch, roll and/or yaw of the head, all of which can be potentially used as inputs to an electronic device. The head gestures can have various meanings depending on application. For example, the same head gesture can initiate a different action in different applications. The sensing used to identify a gesture can be binary or analog. For example, with regards to binary, a head turn may simply change from one state to another. With regards to analog, the movement itself may impact a control function. It should be appreciated that head gestures may be used separately or in combination to provide inputs. The various motions that may be detected include, for example: left tilt, right tilt, back and forth left and right tilt, forward tilt, back tilt, back and forth forward and back tilt, left rotation, right rotation, back and forth right and left rotation, swirling the head in a circle in vertical orientation, swirling the head in a circular manner in a horizontal orientation. The motions may also be distinguished or altered as a function of speed, time, pauses in between, etc. An entire head gesture language may be developed. In one example, a head bobbing can be used in a manner similar to Morse code in order to provide text input commands. Further, "noise" filtering can be provided so as to reduce erroneous detection of gestures during regular head movements. The various gestures can cause inputs (e.g., commands) to an electronic device, such as for an application operating on the electronic device. The inputs can be user selections, user data inputs, scroll, browse, navigation, cursor control, etc.

In one implementation, a scroll, browse or paging action can be initiated or controlled by one or more head gestures. For example, a rotate head or tilt head to right can cause a next item/page action to the right. Subsequently holding ones head in the tilted position can cause the speed of the action to increase until head returns to normal position.

In another implementation, a yes/no input can be provided by a head gesture. For example, if system asks a user of a mobile telephone for input when the mobile telephone is in use, such as when another call comes in, the user can be prompted with a screen that asks whether to skip an incoming call or place current call on hold to answer incoming call. In response, the user could simply reply yes or no as he would in normal conversation. Alternatively, the user could provide one or more head gestures, e.g., back and forth horizontal head movement for a "no" response or back and forth vertical head movement for a "yes" response.

In another implementation, an up or down movement creates vertical scroll event, whereas left or right movement creates horizontal scroll event, and further holding ones head in up, down, left or right position can increase or accelerate the rate of scrolling until the head is moved back to normal In another implementation, a head gesture can be used to acknowledge something. For example, a simple head tilt, may be used as an enter command.

In another implementation, moving the head left can request a "forward: action, and moving the head right can request a "back" action, or vice versa, Alternatively, moving the head upward in the vertical direction can request a "back" action, and moving the head downward in the vertical direction can request a "forward" action.

In another implementation, a left tilt followed by front tilt can request a pick/drag/drop upward left direction on screen. A right tilt followed by front tilt can request a pick/drag/drop upward right direction on screen. A left tilt followed by back tilt can request a pick/drag/drop downward left direction on screen. A right tilt followed by back tilt can request a pick/drag/drop downward right direction on screen.

In another implementation different head positions may be associated with different entries or functions. With regard to data entry, the various head positions may equate to alpha-numeric characters or user interface control for selecting or entering alpha-numeric characters.

In another implementation, a number of movements in a sequence (e.g., successive movements) can signify an entry number or a number of entries by the user. For example, one movement can signify one entry, or entry #1, two movements can signify two entries or entry #2, etc. A different gesture or a pause can cause the user input to be finalized.

In still another implementation, small quick discrete movements may have a first meaning while large exaggerated movements may have a second meaning.

Figure 3:
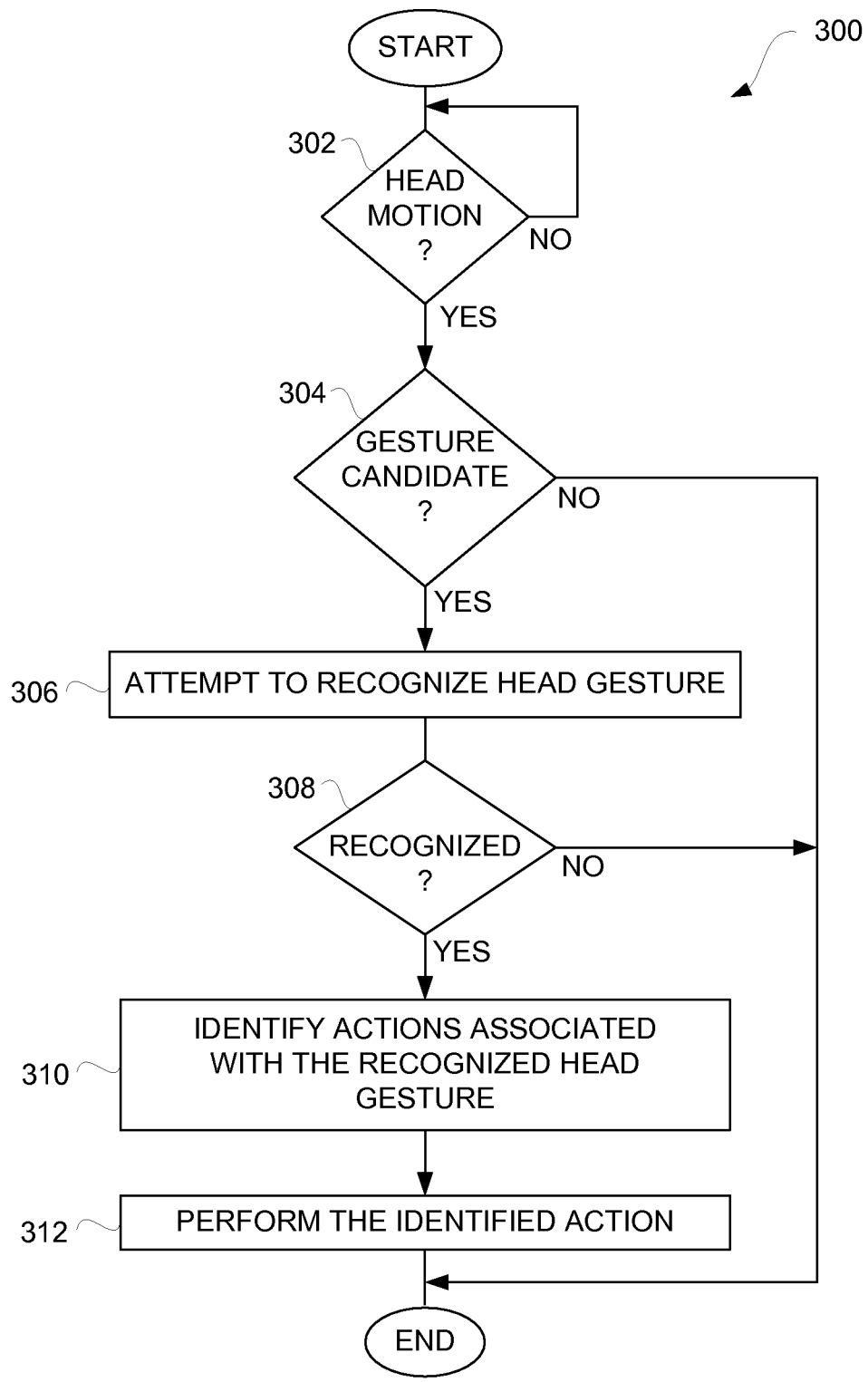
FIG. 3 is a flow diagram of a head gesture process according to one embodiment of the invention.

FIG. 3 is a flow diagram of a head gesture process 300 according to one embodiment of the invention. The head gesture process 300 can, for example, be performed by an electronic device having a monitoring system, such as the electronic device 216 illustrated above in FIG. 2.

The head gesture process 300 can begin with a decision 302 that determines whether a head motion has been detected. When the decision 302 determines that a head motion is not detected, the head gesture process 300 can await a head motion. In other words, the head gesture process 300 operates or is invoked once a head motion is detected. A head motion that is detected can pertain to a head gesture or a random head movement of a user. Though filter processing, the head gesture process can eliminate many random head motions of a user that are not intended to provide a gesture. Hence, once a head motion is detected, a decision 304 can determines whether the head motion corresponds to a gesture candidate.

When the decision 304 determines that the head motion is a gesture candidate, the head gesture process 300 can attempt 306 to recognize the head gesture. A decision 308 can determine whether the head motion is able to be recognized as a head gesture. Here the characteristics of the head motion can be compared with characteristics for a set of predetermined head gestures. If the decision 308 determines that the head motion is able to be recognized as a particular head gesture, an action associated with the recognized head gesture can be identified 310. The action can be a control signal or command for the electronic device. Thereafter, the identified action can be performed 312. After the identified action is performed, the head gesture process 300 can end.

On the other hand, if the decision 308 determines that the head motion is not able to be recognized as a particular head gesture, the blocks 310 and 312 are bypassed and the head gesture process 300 can end. Also, if the decision 304 determines that the head motion is not a gesture candidate, the blocks 306-312 are bypassed and the head gesture process 300 can end. In these situations, the head motion detected does not result in a recognized head gesture or an action performed in response to a recognized head gesture, Additionally, the electronic device can monitor user actions passively and make appropriate decisions, for example, based on user actions or conditions, the electronic device can perform physical monitoring for the user. Examples of physical monitoring can vary. However, one example is that in the electronic device can estimate whether the user is tired, and if so, can induce or motivate the user to continue. As another example, the electronic device can sense when the user is running uphill, and generate the appropriate motivation for the benefit of the user. Some examples of motivation for the user are playback of a motivating song, providing encouraging words, increasing playback tempo of a song being played, etc. U.S. Patent Publication No. 2006/0107822, which is hereby incorporated herein by reference, contains addition information on synchronized song playback in view of user activity.

In one embodiment, although activity monitoring with headphones, earbuds or headsets can be used to control an electronic device (host device), such as a portable media player, the headphones, earbuds or headsets can operate separate from an electronic device. For example, the headphones, earbuds or headsets can include the sensor, processing resources and an energy source (e.g., battery). As one particular usage example, the headphones, earbuds or headsets can itself determine distance traveled and provide a beep or vibration to the user via the headphones, earbuds or headsets at predetermined distances (e.g., every mile). The headphones, earbuds or headsets can be self-actuating based on initial movement or based on a proximity sensor that knows when the earphone is in the user's ear.

In one embodiment, the portable electronic device can also either directly support wireless communication with the monitoring system or sensor or indirectly support wireless communications by using an attachable accessory device that provides wireless capability to the portable electronic device. U.S. Patent Publication No. 2007/0270663, which is hereby incorporated herein by reference, contains addition information on wireless accessory devices.

In one embodiment, the monitoring system can be used, alone or with another electronic device (e.g., media playback device), to provide audio feedback or speech. In one embodiment, the electronic device can support speech recognition so as to be capable of being commanded by user speech commands, alone of in combination with gestures (discussed above).

In still another embodiment of the invention, the activity sensor being utilized above can be combined with other sensor data provided by a monitoring system. The advantage for the monitoring system is that the overall quality of data being received and processed can be increased through use of additional sensors. The presence of the multiple sensors also increases the extent to which other characteristics associated with the user can be monitored and utilized for the benefit of the user. For example, these other characteristics associated with the user can include form, posture or type sporting activity. Further, in one embodiment, using such one or more other characteristics (regardless of how acquired), type of user activity can be determined. Further, when used with a digital media player, the type of activity (or more generally the user characteristics) can be used to set influence media selections for playback by the digital media player.

According to another aspect of the invention, motion and/or directional sensors can be used to determine the direction of the user's gaze. One or more sensors in a user's ear can provide an indication of movement and/or direction that a user is looking or gazing. The sensor can be supplied to an electronic device which can determine the direction the user is looking or gazing. The electronic device, or applications running thereon, can make use of the determined direction. For example, the electronic device (or its display screen) can turned on if the user is looking at the electronic device itself and turned off (or placed in a power saving mode) if the user is not looking at the electronic device, thereby saving valuable battery power. The direction can also be used in combination with GPS data to allow a device/system to know what a user is looking at.

According to another aspect of the invention, a portable electronic device coupled to the monitoring system can monitor, process, present and manage data captured by one or more sensors. The portable electronic device offers a convenient user interface that can be visual and/or audio based customized to a particular application, user-friendly and/or dynamic. The portable electronic device can pertain to a portable media player and thus also provide media playback. U.S. Patent Publication No. 2007/0271065, which is hereby incorporated herein by reference, contains additional information on such a portable electronic device.

In one embodiment, the invention is suitable for use in monitoring sports-related data, such as exercise data (e.g., distance, speed, duration, etc.). However, it should be recognized that the invention is not limited to sports monitoring, but instead is applicable to any type of monitoring. For example, the monitoring can be any physiological monitoring of a person, who is typically the user of a portable electronic device. Still further, according to one embodiment, data monitoring and management can be organized into workouts. A graphical user interface that permits user configuration or user selections, presents menus for workout selection, presents workout status information, and provides workout results. A particular or selected playlist (i.e., a group of songs) can be played during a workout. U.S. Patent Publication No. 2007/0270663, which is hereby incorporated herein by reference, contains addition information on physiological monitoring, and U.S. Patent Publication No. 2007/0271065, which is hereby incorporated herein by reference, contains addition information on organization of workouts.

The various aspects, features, embodiments or implementations of the invention described above can be used alone or in various combinations.

The many features and advantages of the present invention are apparent from the written description. Further, since numerous modifications and changes will readily occur to those skilled in the art, the invention should not be limited to the exact construction and operation as illustrated and described. Hence, all suitable modifications and equivalents may be resorted to as falling within the scope of the invention.

What is claimed is:

1. A hearing device, comprising:
   an audio output device configured to be positioned within a user's ear;
   a monitoring system located in substantially close proximity to the audio output device, the monitoring system including:
      an activity sensor housed in the audio output device and configured to detect head motion data; and
      a biometric sensor housed in the audio output device and configured to monitor biometric data pertaining to the user,
   wherein said monitoring system is configured for:
      receiving the head motion data from the activity sensor;
      determining whether the head motion data matches a predetermined head gesture;
      identifying a first action associated with the matching predetermined head gesture;
      receiving biometric data from the biometric sensor;
      determining whether the biometric data matches a predetermined physical characteristic;
      identifying a second action associated with the matching physical characteristic; and
      performing the first identified action or the second identified action on a portable electronic device in communication with the hearing device.

2. A hearing device as recited in claim 1, wherein said audio output device comprises a speaker.

3. A hearing device as recited in claim 1, wherein said hearing device is an earbud, a headset or headphones.

4. A hearing device as recited in claim 1, wherein said hearing device further comprises:
   a cord coupled to said audio output device, and
   wherein said monitoring system is attached to said cord.

5. A hearing device as recited in claim 1, wherein said monitoring system is configured to monitor one or more of temperature, perspiration or heart rate pertaining to the user.

6. A hearing device as recited in claim 1,
   wherein said hearing device is coupled to an electronic device that provides audio signals that are supplied to said audio output device.

7. A hearing device as recited in claim 6, wherein the electronic device is a mobile device having media playback capability.

8. A hearing device as recited in claim 7, wherein said hearing device is responsive to movement of the user's head to invoke commands for the mobile device.

9. A hearing device as recited in claim 7, wherein said hearing device is responsive to a predetermined movement of the user's head to invoke commands for the media playback device.

10. A hearing device as recited in claim 7, wherein said hearing device is a wearable hearing device.

11. A hearing device as recited in claim 7, wherein the electronic device is configured to supply audio signals associated with the user's biometric data or movement data obtained from the monitoring system.

12. A hearing device as recited in claim 9, wherein the predetermined movement is a gesture using the user's head.

13. A hearing device as recited in claim 1, wherein said monitoring system is internal to said audio output device.

14. A hearing device as recited in claim 1, wherein said monitoring system is integral to said audio output device.

15. A hearing device as recited in claim 1, wherein said monitoring system is removably attached to said audio output device.

16. An earbud for use by a user to receive audio sound, said earbud comprising:
   an upper portion;
   an ear interface portion positioned proximate the upper portion, the ear interface portion configured to be placed within or proximate to the ear of the user;
   a speaker housed within the upper portion and configured to produce audible sound that is provided to the ear of the user via said ear interface portion; and
   an activity sensor coupled to the upper portion, the activity sensor including:
      at least one accelerometer configured to monitor user activity, wherein the at least one accelerometer is configured to detect user movements or gestures; and at least one biometric sensor configured to monitor biometric data pertaining to the user, wherein the earbud is configured for:
- receiving the head motion data from the activity sensor;
- determining whether the head motion data matches a predetermined head gesture;
- identifying a first action associated with the matching predetermined head gesture;
- receiving biometric data from the biometric sensor;
- determining whether the biometric data matches a predetermined physical characteristic;
- identifying a second action associated with the matching physical characteristic; and
- performing the first identified action or the second identified action on a portable electronic device in communication with the hearing device.

17. An earbud as recited in claim 16, wherein said activity sensor is removable from said earbud.

18. An earbud as recited in claim 16, wherein the activity sensor is housed within the upper portion.

19. A method for controlling a portable electronic device through one or more head gestures, said method comprising:
- receiving head motion data from an activity sensor housed within a hearing device positioned proximate to an ear of the user, the head motion data pertaining to a head motion of a user of the electronic device;
- determining whether the head motion data matches any of a plurality of predetermined head gestures;
- identifying a first action associated with the matching predetermined head gesture;
- receiving biometric data from a biometric sensor housed within the hearing device positioned proximate to an ear of the user;
- determining whether the biometric data matches any of a plurality of predetermined physical characteristics;
- identifying a second action associated with the matching physical characteristics; and
- performing the first identified action or the second identified action on the portable electronic device.

20. A method as recited in claim 19, wherein said portable electronic device is a mobile device having media playback capability.

* * * * *